United States Patent
Kuusela et al.

(10) Patent No.: US 10,188,873 B2
(45) Date of Patent: Jan. 29, 2019

(54) SYSTEMS AND METHODS FOR DOSE CALCULATION IN GENERATING RADIATION TREATMENT PLANS

(71) Applicant: Varian Medical Systems International AG., Cham (CH)

(72) Inventors: Esa Kuusela, Espoo (FI); Janne Nord, Espoo (FI); Joakim Pyyry, Helsinki (FI); Perttu Niemela, Espoo (FI)

(73) Assignee: Varian Medical Systems International AG, Cham (CH)

( * ) Notice: Subject to any disclaimer, the term of this patent is extended or adjusted under 35 U.S.C. 154(b) by 103 days.

(21) Appl. No.: 15/466,451

(22) Filed: Mar. 22, 2017

(65) Prior Publication Data

US 2018/0272152 A1  Sep. 27, 2018

(51) Int. Cl.
*G06K 9/00* (2006.01)
*A61N 5/10* (2006.01)
*G06T 7/00* (2017.01)

(52) U.S. Cl.
CPC ......... *A61N 5/1031* (2013.01); *A61N 5/1036* (2013.01); *A61N 5/1038* (2013.01); *G06T 7/0012* (2013.01); *A61N 5/1045* (2013.01); *A61N 2005/1041* (2013.01)

(58) Field of Classification Search
CPC .......... A61N 5/1031; A61N 2005/1041; A61N 5/103; A61N 2005/1074; A61N 2005/1087; A61N 5/1047; A61N 2005/1032; A61N 2005/1089; A61N 2005/1091; A61N 5/1081; A61N 5/10; A61N 5/1039; A61N 5/1042; A61N 5/1043; A61N 5/1048
See application file for complete search history.

(56) References Cited

U.S. PATENT DOCUMENTS

| | | | | |
|---|---|---|---|---|
| 5,394,452 A | * | 2/1995 | Swerdloff | A61N 5/1042 378/150 |
| 5,724,400 A | * | 3/1998 | Swerdloff | A61B 6/00 378/150 |
| 9,901,749 B2 | * | 2/2018 | Van Heteren | A61N 5/1031 |
| 2009/0154644 A1 | * | 6/2009 | Nord | A61N 5/103 378/65 |
| 2009/0326615 A1 | * | 12/2009 | Nord | A61N 5/103 607/88 |
| 2010/0054410 A1 | * | 3/2010 | Nord | A61N 5/1031 378/65 |
| 2010/0177871 A1 | * | 7/2010 | Nord | A61N 5/103 378/65 |
| 2010/0232572 A1 | * | 9/2010 | Nord | A61N 5/103 378/65 |

(Continued)

FOREIGN PATENT DOCUMENTS

WO  WO2014139040 A2  9/2014

*Primary Examiner* — Avinash Yentrapati (57) ABSTRACT

A first dose calculated using a first set of fluence maps and a first (faster) dose prediction model is accessed. A second fluence map is accessed. The second fluence map is projected onto the first set of fluence maps to deter me set of scalars and a residual value. When the residual value satisfies a criterion, a second dose is calculated using the first dose prediction model, the set of scalars, and the second fluence map. When the residual value does not satisfy the criterion, the second dose is calculated using a second (more accurate) dose prediction model and the second fluence map.

20 Claims, 6 Drawing Sheets

(56) References Cited

U.S. PATENT DOCUMENTS

| | | | | |
|---|---|---|---|---|
| 2012/0014507 | A1* | 1/2012 | Wu | A61N 5/10 |
| | | | | 378/65 |
| 2013/0197878 | A1* | 8/2013 | Fiege | A61N 5/1031 |
| | | | | 703/2 |
| 2014/0072109 | A1* | 3/2014 | Van Heteren | A61N 5/1031 |
| | | | | 378/208 |
| 2014/0279725 | A1* | 9/2014 | Kuusela | A61N 5/103 |
| | | | | 706/11 |
| 2014/0350863 | A1* | 11/2014 | Hartman | A61N 5/1031 |
| | | | | 702/19 |
| 2015/0095043 | A1* | 4/2015 | Cordero Marcos | A61N 5/1031 |
| | | | | 705/2 |
| 2017/0189715 | A1* | 7/2017 | Isola | A61N 5/1031 |
| 2017/0296840 | A1* | 10/2017 | Bokrantz | A61N 5/1045 |
| 2017/0340900 | A1* | 11/2017 | Moore | A61N 5/1031 |
| 2018/0043182 | A1* | 2/2018 | Wu | G06Q 50/24 |

* cited by examiner

402
GENERATE A FLUENCE MAP

↓

404
PERFORM FLUENCE OPIMIZATION

502
CONVERT AN INITIAL CONTROL POINT SEQUENCE INTO A 2D FLUENCE MAP

↓

504
CALCULATE DOSES BASED ON THE FLUENCE MAP USING A FIRST DOSE PREDICTION MODEL; ITERATE TO GENERATE FINAL FLUENCE MAPS

↓

506
CALCULATE DOSES BASED ON THE FINAL FLUENCE MAPS USING A SECOND DOSE PREDICTION MODEL

↓

508
CALCULATE DIFFERENCES BETWEEN THE DOSES CALCULATED WITH THE FIRST DOSE PREDICTION MODEL AND THE DOSES CALCULATED WITH THE SECOND PREDICTION MODEL

↓

510
GENERATE/ACCESS A NEW FLUENCE MAP

Fig. 6

SYSTEMS AND METHODS FOR DOSE CALCULATION IN GENERATING RADIATION TREATMENT PLANS

RELATED U.S. APPLICATIONS

This application is related to the U.S. application Ser. No. 15/403,955, filed Jan. 11, 2017, entitled "Systems and Methods for Generating Radiation Treatment Plans," and to the U.S. application Ser. No. 15/391,058, filed Dec. 27, 2016, entitled "Selecting a Dose Prediction Model Based on Clinical Goals," both of which are hereby incorporated by reference in their entirety.

BACKGROUND

The use of radiation therapy to treat cancer is well known. Typically, radiation therapy involves directing a beam of high energy proton, photon, or electron radiation ("therapeutic radiation") into a target volume a (e.g., a tumor or lesion).

Before a patient is treated with radiation, a treatment plan specific to that patient developed. The plan defines various aspects of the therapy using simulations and optimizations based on past experiences. For example, for intensity modulated radiation therapy (IMRT), the plan can specify the appropriate beam type (e.g., flattening filter free type) and the appropriate beam energy. Other parts of the plan can specify, for example, the angle of the beam relative to the patient, the beam shape, the placement of boluses and shields, and the like. In general, the purpose of the treatment plan is to deliver sufficient radiation to the target volume while minimizing exposure of surrounding healthy tissue to the radiation.

In IMRT, the planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is best suited to achieving the desired outcome.

For example, the planner defines a set of quality metrics, such as target homogeneity, critical organ sparing, and the like, and respective target values $Q_i$ for the metrics. For planning, the metrics are defined such that a smaller value is preferred over a larger value. The planner also defines a relative priority or weight $w_i$ for each of the quality metrics. The task of developing an optimal plan is then formulated as a quadratic cost function C: $C=sum(w_i(Q_i(Q_i-q_i)^2)$, where $q_i$ is the value of the quality metric that can be achieved for a particular treatment plan. The optimal plan is determined by minimizing the cost function C.

Often it is not easy to determine, an optimal plan based solely on the cost function. For instance, the optimal solution of the cost function may not necessarily describe the clinically best balance between quality metrics, or the dose distribution might have some undesirable features that are difficult to represent as a quality metric.

One way to assist the planner is a knowledge-based approach that automatically generates objective functions so that the resulting plan incorporates and reflects present practices utilized in creating the knowledge base. This typically captures the best practices utilized at a treatment center, but can also be based on larger knowledge bases of well-defined treatments gathered from multiple treatment centers.

Another way to assist the planner is to use a multi-criteria optimization (MCO) approach for treatment planning. Pareto surface navigation is an MCO technique that facilitates exploration of the tradeoffs between clinical goals. For a given et of clinical goals, a treatment plan is considered to be Pareto optimal if it satisfies the goals and none of the metrics can be improved without worsening at least one of the other metrics. The set of Pareto optimal plans define a Pareto surface related to the set of clinical goals. Movement along the Pareto surface results in tradeoffs between the clinical goals; some metrics will improve at the cost of worsening one or more other metrics. The planner can navigate along the Pareto surface and choose a final (optimized) radiation treatment plan that seems to be the best according to the criteria applied b the planner, or a treatment plan can be selected automatically based on its proximity to the Pareto surface.

Navigation n the vicinity of the Pareto surface requires that a well-selected sample set of plans has been generated to define the Pareto surface. To maintain fluent interactivity during the navigation, the plans are calculated beforehand, and thus an educated guess must first be made about the region where the planner wants to navigate, so that the Pareto surface spans that region. If, during navigation, the planner wants to move beyond the region spanned by the original sample set of plans, then it is possible to enlarge the sample set by generating and adding more plans. In such cases, it is desirable that the additional plans be generated quickly.

A methodology that efficiently and quickly generates additional plans would be valuable.

SUMMARY

Embodiments according to the present invention provide a methodology that efficiently and quickly generates additional radiation treatment plans, in particular by efficiently and quickly perform g dose calculations.

In an embodiment, a value for a first d case calculated using a first set of fluence maps and a first (faster) dose prediction model is accessed. A second fluence map is accessed. The second fluence map projected onto the first set of fluence maps to determine a set of scalars and a residual value. When the residual value satisfies a criterion, a second dose is calculated using the first dose prediction model, the set of scalars, and the second fluence map. When the residual value does not satisfy the criterion, the second dose is calculated using a second (more accurate) dose prediction model and the second fluence map.

A final radiation treatment plan is selected from a sample set of treatment plans that includes at least a first radiation treatment plan based on the first set of fluence maps and a second radiation treatment plan based on the second fluence map.

The ability to use the first (faster) dose prediction model in lieu of the second (more accurate but slower and more resource-intensive) dose prediction model means that additional radiation treatment plan can be quickly and efficiently generated.

Thus, embodiments according to the invention improve the field of radiation treatment planning specifically and the field of radiation therapy in general. In IMRT, beam intensity is varied across each treatment region (target volume in a patient. Instead of being treated with a relatively large and uniform beam the patient is treated with many smaller beams (e.g., pencil beams or beamlets), each of which can have its own intensity, and each of which can be delivered from a different angle (which may be referred to as beam geometry). Because of the many possible beam geometries, the number of beams, and the range of beam intensities, there is effectively an infinite number of potential treatment plans, and therefore consistently and efficiently generating and evaluating high-quality treatment plans is beyond the capability of a human and requires the use of a computing system, particularly considering the time constraints associated with the use of radiation therapy to treat ailments like cancer, and particularly considering the large number of patients that are undergoing or need to undergo radiation therapy during any given time period. Embodiments according to the invention allow more effective treatment plans to be generated quickly, which can be of critical importance considering the urgency of beginning radiation therapy when a patient is diagnosed with a disease such as cancer. Also, embodiments according to the invention help improve the functioning of computing systems because fewer computational resources are needed and consumed to develop a plan, meaning also that computer resources are freed up to perform other tasks.

This summary is provided to introduce a selection of concepts in a simplified form that is further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents which may be included within the spirit and scope of the disclosure as defined by the appended claims. Furthermore, in the following detailed description of the present disclosure numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "executing," "accessing," "calculating," "projectings," "summing," "selecting," "converting," "generating," "comparing," or the like, refer to actions and processes (e.g., the flowcharts of FIGS. 4, 5A, 5B, and 6) of a computing system or similar electronic computing device or processor (e.g., the computing system 100 of FIG. 1). The computing system or similar electronic computing device manipulates and transforms data represented as physical (electronic) quantities within the computing system memories registers or other such, information storage, transmission or display devices. Terms such as "dose" or "fluence" generally refer to dose or fluence value; the use of such terms will be clear from the context of the surrounding discussion.

Portions of the detailed description that follows are presented and discussed in terms of a method. Although steps and sequencing thereof are disclosed in figures herein (e.g., FIGS. 4, 5A, 5B, and 6) describing the operations of this method, such steps and sequencing are exemplary. Embodiments are well suited to performing various other steps or variations of the steps recited in the flowchart of the figure herein and in a sequence other than that depicted and described herein.

Embodiments described herein may be discussed in the general context of computer-executable instructions residing on some form of computer-readable storage medium such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks of implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, date structures, program modules or other data. Computer storage media includes, but is not limited to, random access memory (RAM), read only memory (ROM), electrically erasable programmable ROM (EEPROM) flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RE), infrared and other wireless media. Combinations of any of the above can also be included within the scope of computer read able media.

Figure 1:
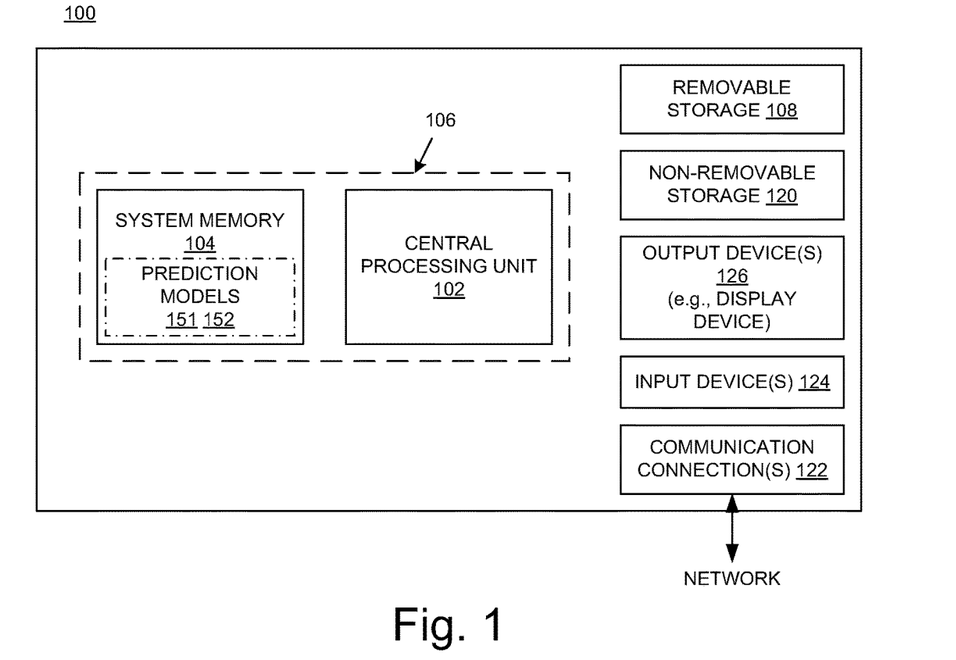
FIG. 1 shows a block diagram of an example of a computing system upon which the embodiments described herein may be implemented.

FIG. 1 shows a block diagram, of an example of a computing system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such a keyboard, mouse, pen, voice input device, touch input device, etc. Output devices) 126 such as a display device, speakers, printer, etc., are also included.

As will be explained further below, embodiments according to the invention utilize two dose prediction models 151 and 152. In the example of FIG. 1, the memory 104 includes computer-readable instructions, data structures, program modules, and the like associated with the dose calculation models or dose prediction models 151 and 152. However, the dose prediction models 151 and 152 may instead reside in any one of the computer storage media used by the system 100 or may be distributed over some combination of the computer storage media, or may be distributed over some combination of networked computers.

The dose prediction model 151 (also referred to herein as the first prediction model) executes faster than and requires fewer computational resources, but is less accurate than, the dose prediction model 152 (also referred to herein as the second prediction model). When and how each of the dose prediction models is used is discussed further below in conjunction with FIGS. 5A and 5B.

The dose prediction models 151 and 152 may be used to predict dose parameters for a treatment plan corresponding to a particular patient. The dose prediction models 151 and 152 may be implemented as a dose-volume histogram (DVH) estimation model for a region of interest (ROI), where the predicted quantity is a dose volume histogram. The ROI is a three-dimensional (3D) volume in the patient that contains the target volume as any nearby structures (organs) that might be adversely affected by radiation. In other embodiments the prediction models 151 and 152 also generate a prediction based on a distance to a target (DTH) histogram, which expresses the distance an ROI to a radiation target. In yet other embodiments, the dose prediction models 151 and 152 are implemented as any other model suitable for predicting (calculating) doses (as a dose histogram or spatial 3D dose distribution) for a radiation treatment plan.

The dose prediction models 151 and 152 can then be used to develop a radiation treatment plan for a particular patient by receiving patient-specific information (e.g., geometry information) that is input to and processed by the model. The input patient-specific information may contain any combination of parameters that can practically affect the radiation treatment plan. For example, the patient-specific information may be or organized as a vector or a data structure including feature elements for: size and shape of the target volume; location of the target volume; size and shape of an organ at risk; type of an organ at risk; a part of the target volume that overlaps an organ; and a part of an organ that overlaps the target volume.

Figure 2:
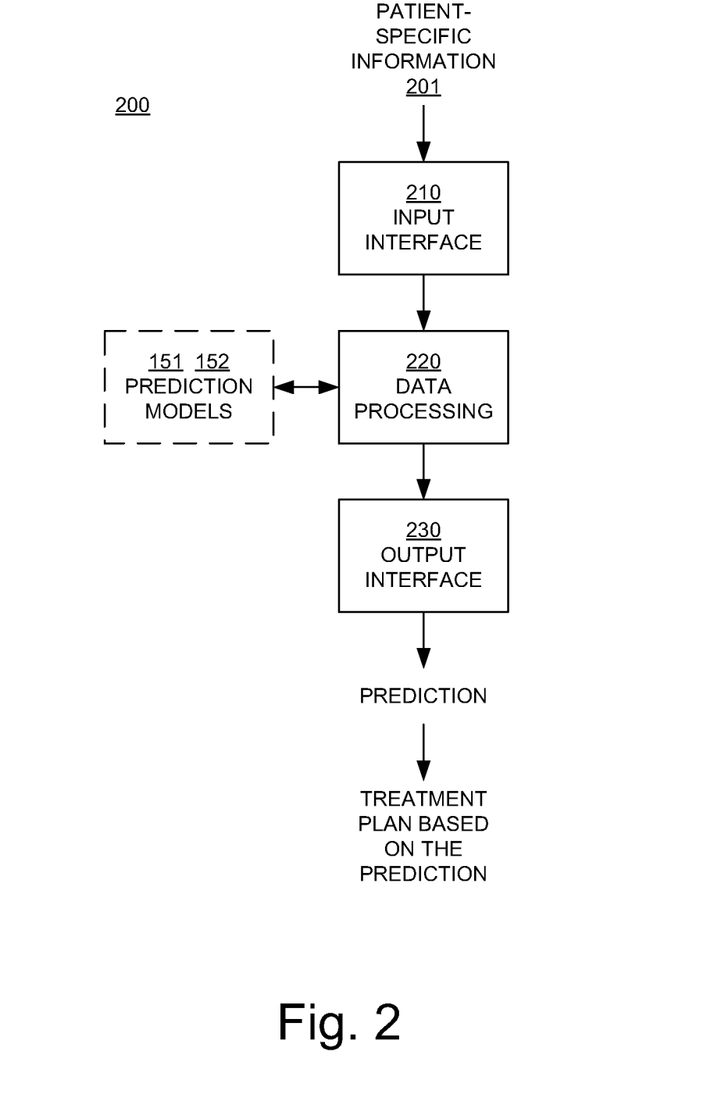
FIG. 2 is a block diagram illustrating an example of an automated radiation treatment planning system in an embodiment according to the present invention.

FIG. 2 is a block diagram illustrating an example of an automated radiation therapy treatment planning system 200 in an embodiment according to the present invention. The system 200 includes an input interface 210 to receive patient-specific information (data) 201, a data processing component 220 that implements the prediction models 151 and 152, and an output interface 230. The system 200 in whole or in part may be implemented as a software program hardware logic, or a combination thereof on/using the computing system 100 (FIG. 1).

The patient-specific information is provided to and processed by the prediction models 151 and 152. The prediction models 151 and 152 yield a prediction result, e.g., an achievable dose distribution prediction. A treatment plan based on the prediction result can then be generated. In an embodiment, the prediction result is accompanied by parameters indicative of the quality of the prediction, such as reliability of the result (e.g., affected by the internal coherence of the training data), complexity of the predicted plan, and probability of the result.

Figure 3:
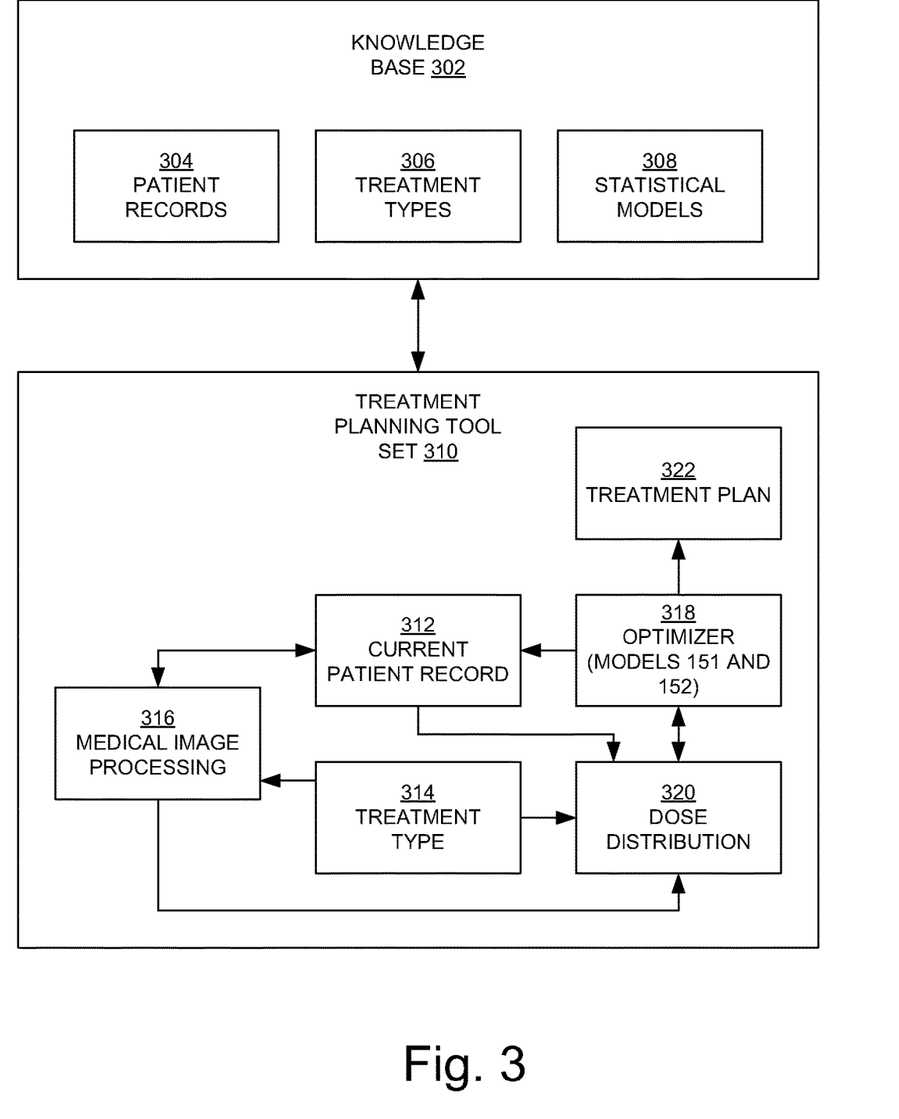
FIG. 3 illustrates an embodiment of a knowledge-based planning system in an embodiment according to the present invention.

FIG. 3 illustrates an embodiment of a knowledge-based planning system 300 incorporating a combination of patient records and statistical models for generating radiation treatment plans in an embodiment according to the present invention. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, an optimizer 318, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322. A radiation treatment plan developed in this manner (e.g., the treatment plan 322) can be referred to as a balanced plan.

More specifically based on past clinical experience, when a patient presents with a particular diagnosis, stage, age, weight, sex, co-morbidities, etc., there can be a treatment type that is used most often. By selecting the treatment type that the planner has used in the past for similar patients, a first step treatment type 314 can be chosen. The medical image processing module 316 provides automatic contouring and automatic segmentation of two-dimensional cross-sectional slides (e.g., from computed tomography or magnetic resonance imaging) to form a 3D image using the medical images in the current patient record 312. Dose distribution maps are calculated by the dose distribution module 320, which may utilize the dose prediction models 151 and 152 of the optimizer 318.

The knowledge base 302 can be searched for a combination of objectives that can be applied by the optimizer 318 to determine a dose distribution. For example, an average organ-at-risk dose-volume histogram, a mean cohort organ-at-risk dose-volume histogram, and average organ-at-risk objectives can be selected from the knowledge base 302. In embodiments according to the present invention, the optimizer 318 uses the dose prediction models 151 and 152 to help shape the dose distribution. Accordingly, the optimizer 318 can provide a 3D dose distribution, fluences, and associated dose-volume histograms for the current patient. By using the dose prediction models 151 and 152, those results are expected to fall within the historically accepted range for a patient with a similar disease type and treatment type.

FIGS. 4, 5A, 5B, and 6 are flowcharts 400, 500, and 600, respectively, of examples of computer-implemented methods for generating a radiation treatment plan in embodiments according to the present invention. The flowcharts 400, 500, and 600 can be implemented as computer-executable instructions residing on some form of computer-readable storage medium (e.g., using the computing system 100 of FIG. 1).

In IMRT, beam intensity is varied across and treatment region (target volume) in a patient. Instead of being treated with a relatively large and uniform beam, the patient is treated with many smaller beams (e.g., pencil beams or beamlets), each of which can have its own intensity, and each of which can be delivered from a different angle (which may be referred to as beam geometry). Because of the many possible beam geometries, the number of beams, and the range of beam intensities, there is effectively an infinite number of potential treatment plans, and therefor consistently and efficiently generating and evaluating high-quality treatment plans is beyond the capability of a human and requires the use of a computing system, particularly considering the time constraints associated with the use of radiation therapy to treat ailments like cancer, and particularly considering the large number of patients that are undergoing or need to undergo radiation therapy during any given time period.

A radiation treatment system for IMRT includes a number of components including, for example, a linear accelerator that delivers a beam (beamlet) of high energy proton, photon, or electron radiation that is modulated using a multileaf collimators (MLC). Each MLC leaf can be independently moved back-and-forth by a computer to dynamically shape an aperture through which the beam can pass, to block or not block portions of the beam and thereby control beam shape and exposure time.

Figure 4:
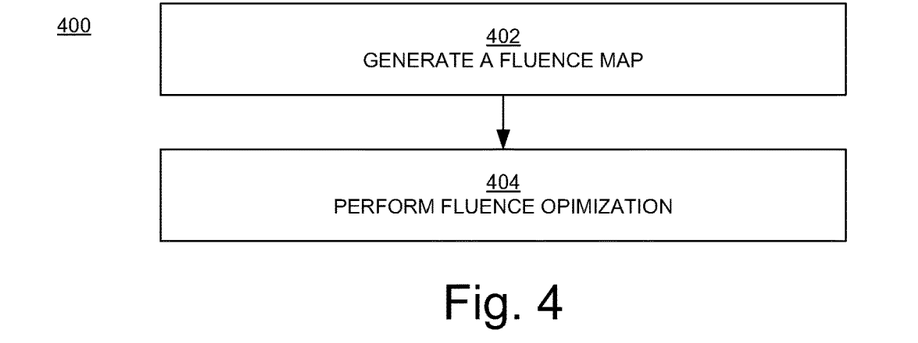
FIGS. 4, 5A, 5B, and 6 are flowcharts of examples of computer-implemented methods for generating a radiation treatment plan embodiments according to the present invention.

In block 402 of FIG. 4, a fluence map is generated. In general a control point sequence selected or generated, defining how the radiation treatment system is to deliver the required doses to the patient/target volume. The control point sequence can be selected using the knowledge-based planning system 200 of FIG. 3.

A control point sequence can include, for example, settings (leaf sequence settings) that control movement of the MLC during radiation treatment. A control point sequence can be converted into a two-dimensional (2D) fluence map that represents the intensity of the beam passing through the MLC aperture per unit of time.

In block 404 of FIG. 4, fluence optimization is performed, to optimize the individual components of the fluence map to produce the best radiation treatment plan for treating the patient. The ROI can be divided into smaller 3D element known as voxels. Each voxel will receive a dose of radiation that can be predicted using the 2D fluence map. Each voxel will receive radiation from on or more beamlets delivered from different directions. The total dose for a voxel is the sure of the doses delivered by each beamlet received by the voxel.

The 3D dose (dose per voxel) is a liner function of the fluence maps, meaning that if dose is presented as a function of fluence D(F), then D(F) will satisfy the following relationships: $D(aF)=aD(F)$; and $D(F1+F2)=D(F1)+D(F2)$, where "a" scalar and F1 and F2 are fluence maps.

As mentioned above, in IMRT, the planner's goal is to find a solution that is optimal with respect to multiple clinical goals that may be contradictory in the sense that an improvement toward one goal may have a detrimental effect on reaching another goal. These tradeoffs lead to an iterative prosess in which the planner creates different plans, which can then be evaluated using an MCO approach. Using MCO, the planner can choose a final (optimized) radiation treatment plan that seems to be the best.

Figure 5A:
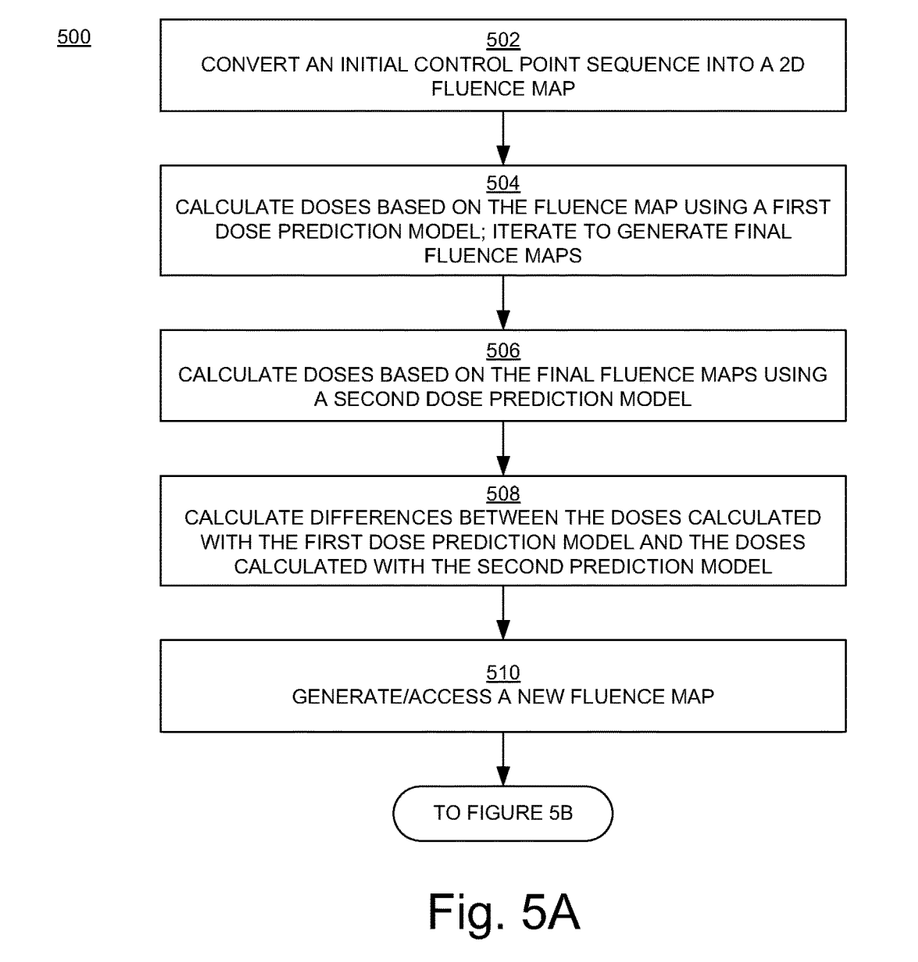
Figure 5B:
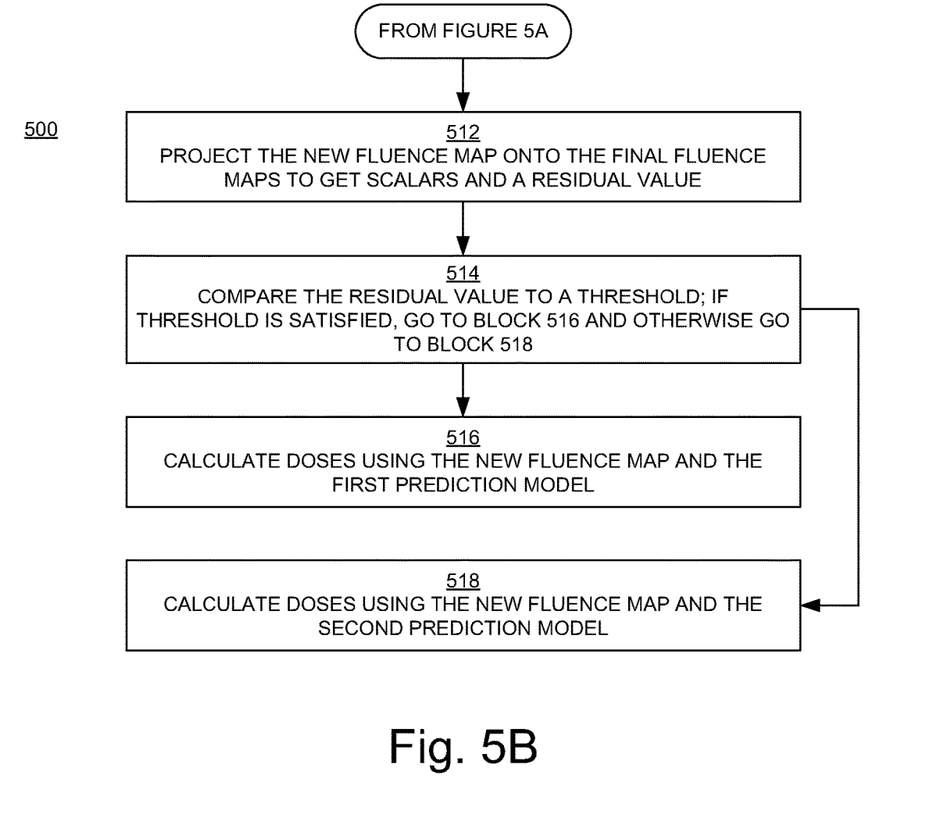

A set of plans is generated as defined above and a well-selected sample set of those plans is used to define a Pareto surface for MCO. With reference to FIGS. 5A and 5B, the generation of a treatment plan is further described.

In block 502, as described above, an initial control point sequence is converted into a 2D fluence map F sequence.

In block 504, doses (e.g., per voxel) based on the fluence map F are calculated using the first dose prediction model 151 (FIG. 1). As mentioned above, the first dose prediction model 151 is characterized as a faster but less accurate model than the second dose prediction model 152. The first dose prediction model 151 is designated herein as D1 and the doses calculated using that model and the fluence maps F are designated herein in the form of D1(F).

The operations described by block 504 are iteratively repeated until a final (optimal) fluence map Fo,1 is generated using D1, the first dose prediction model 151. Those operations are then repeated for n different cost functions to obtain a set of fluence maps Fo. Thus, Fo consist n fluence maps: Fo,1, Fo,2, . . . , Fo,n, where n is the number of cost functions that are considered.

In block 506, doses based on the fluence maps Fo (Fo,1, Fo,2, . . . , Fo,n) are calculated using the second (more accurate) dose prediction model 152. The second dose prediction model 152 is designated herein as D2 and the doses calculated using that model and the fluence maps F are designated herein in the form of D2(F).

In block 508, the differences between the doses calculated using the dose prediction model 151 (in block 504) and the doses calculated using the dose prediction model 152 (in block 506) are calculated. The differences are referred to herein as De: $De=D2(F)-D1(F)$. In the example of FIGS. 5A and 5B, $De=D2(Fo)-D1(Fo)$.

At this point, the fluence maps Fo (Fo,1, Fo,2, . . . , Fo,n) have been determined, the doses D2(Fo) (D2(Fo,1), D2(Fo, 2), ..., D2(Fo,n)) have been calculated, and the differences De (De(Fo,1), De(Fo,2), ..., De(Fo,n)) have been calculated.

In this manner, a radiation treatment plan is generated (this plan may be referred to herein as the first radiation treatment plan: the term "first" does not necessarily mean that it is the initial plan and instead is used simply as a differentiator). The operations just described can be repeated to generate any number of radiation treatment plans to provide a well-selected sample set of plans that can be used to define a Pareto surface.

In block 510, in order to expand the set of treatment plans, another fluence map Fp is generated or accessed. In an embodiment, the fluence map Fp can be generated using a new control point sequence In block 512, the fluence map Fp is projected onto the set of fluence maps Fo: Fp=(a1*Fo,1*a2*Fo,2+. . . + an*Fo, n)+Fr, where a1, a2, ..., an are scalars and Fr is a map of residual fluence values. The operation of determining the scalars is referred to as projecting, and a1*Fo,1 is a projection of Fp in Fo,1 (for example).

The scalers a1, a2, ..., an are chosen so that Fr is as small as possible. In practice, this means that the squared sum of all of the pixels in Fr is small as possible; in linear algebra terminology, the squared length of Fr is minimized.

As mentioned above, the 3D dose (dose per voxel) is a linear function of the fluence maps. Thus, in general De(a1*F1+a2*F2+. . . + an*Fn)=a1*De(F1)+a2*De(F2)+. . . + an*De(Fn).

In block 514, the size (magnitude) of Fr is used to determine whether De(Fp) (D2(Fp)–D1(Fp)) can be approximated satisfactorily using a1*De(Fo,1)+a2*De(Fo,2)+. . . + an*De(Fo,n). More specifically Fr is compared to a threshold value. The threshold value can be a fixed value or it can be scaled (normalized) to the size of Fp. In an embodiment, the threshold value is expressed as:

$$Fr * \frac{\Sigma_i |De(Fp_i)|}{\Sigma_i |Fr|},$$

where "| |" indicates a selected error measure for dose and fluence (e.g., the length in linear algebra).

If Fr satisfies the threshold value (e.g., if Fr is small enough) then the flowchart 500 proceeds to block 516; otherwise, the flowchart proceeds to block 518.

In block 516, if Fr satisfies the threshold value, then the dose D(Fp) based on the fluence map Fp is calculated using the first (faster) dose prediction model 151 (D1) and also using the set of scalars a1, a2, ..., an.

More specifically, in an embodiment, the doses D2(Fo) (D2(Fo,1), D2(Fo,2) ..., D2(Fo,n)), which were calculat using the second (more accurate) dose prediction model 152 and the fluence maps Fo (Fo,1, Fo,2, ..., Fo,n) in block 506, are accessed. In this embodiment, the dose D(Fp) based on the fluence map Fp is then calculated by: a) calculating the dose D1(Fr) based on the fluence map Fr and using the first dose prediction model 151; b) multiplying the scalars a1, a2, ..., an and the doses D2(Fo); and c) summing the results: D(Fp)=D1(Fr)+a1*D2(Fo,1)+a2*D2(Fo,2)+. . . + an*D2(Fo,n).

In another embodiment, the differences De (De(Fo,1), De(Fo,2), ..., De(Fo,n)), which were calculated in block 508, are accessed. In this embodiment, the dose D(Fp) based on the fluence map Fp is then calculated by: a) calculating the doses D1(Fp) based on the fluence map Fp and using the first dose prediction model 151; b) multiplying the scalers a1,a2, . . . , an and the differences De (De(Fo,1), De(Fo,2), ..., De(Fo, n)); and c) summing the results; D(Fp)=D1(Fp)+a1*De(Fo,1)+a2*De(Fo,2)+. . . + an*De (Fo, n).

In block 518, if Fr does no satisfy the threshold value, then the dose D(Fp) for the new treatment plan is calculated using the second dose prediction model 152 (D2).

Thus, in block 516, doses for the new treatment plan can be approximated using first (faster) dose prediction model 151 instead of the second (more accurate) dose prediction model 152. Other treatment plans can be similarly generated. The projection of the new fluence map onto the previous fluence maps determines scalars that weight the previous maps and also determines a residual value that can be used to evaluate the error associated with the approximation, to determine which dose prediction model is to be used. Accordingly, dose results previously calculated for another plan using the more accurate model are used to get a fast first order correction to a new plan that close to the other plan. Computational resources are saved, and the sample plan set can be more quickly expanded.

Figure 6:
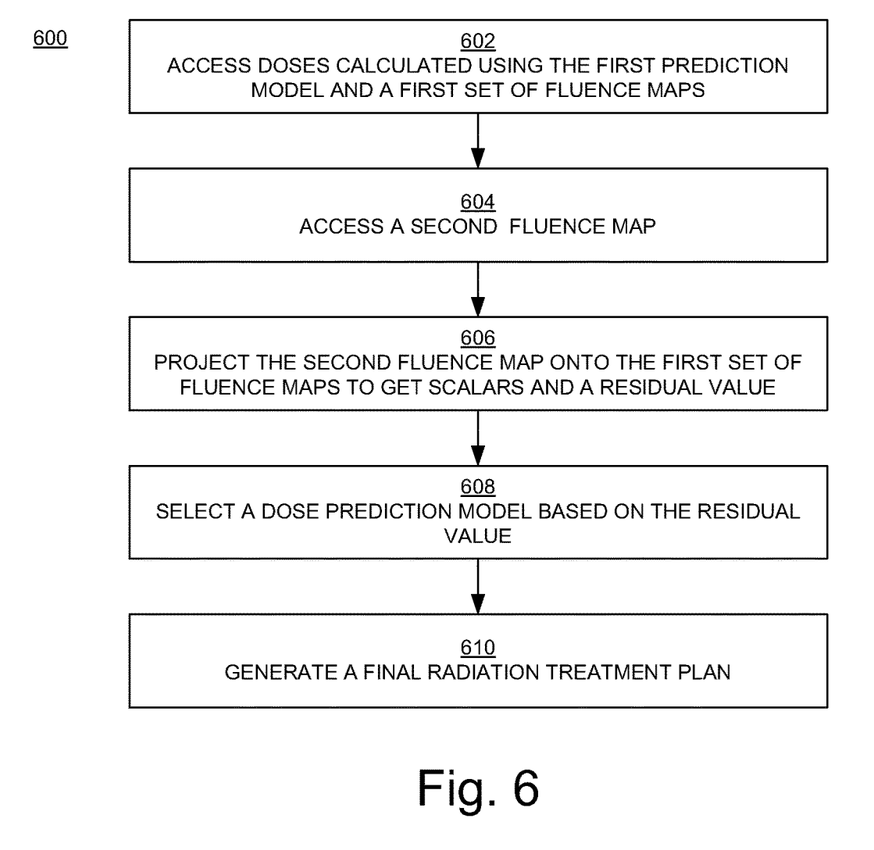

Referring now to FIG. 6, in block 602, first doses (D1 (Fo,1), D1(Fo,2), ..., D1(Fo,n)) are accessed (e.g., from memory) or are calculated using the first dose prediction model 151 (D1) and a first of fluence maps (Fo,1, Fo,2, ..., Fo,n).

In block 604, a second fluence map Fp is accessed (e.g., from memory) or generated.

In block 606, the second fluence map Fp is projected onto the first set of fluence maps Fo to determine a set of scalars a1, a2, ..., an and a residual value Fr: Fp=(a1*Fo,1+a2*Fo, 2+. . . + an*Fo,n)+Fr.

In block 608, a dose prediction mod& is selected based on the residual value. When the residual value satisfies a criterion, a second dose (D(Fp) is calculated using the first dose prediction model 151 (D1), the set of scalars, and the second fluence map Fp. When the residual value does not satisfy the criterion, the second dose D(Fp) is calculated using the second dose prediction model 152 (D2) and the second fluence map Fp.

More specifically, in an embodiment, to calculate the second dose D(Fp), third doses D2(Fo) (D2(Fo,1), D2(Fo,2), ..., D2(Fo,n)) that were calculated using the first set of fluence maps Fo and the second dose prediction model 152 are accessed. A fourth dose D1 (Fr) is calculated using the first dose prediction model 151 and the residual value Fr, and the fourth dose is summed with the products of multiplying the set of scalars and the set of third doses to calculate the second dose: D(Fp)=D1(Fr)+a1*D2(Fo,1)+a2*D2(Fo, 2)+. . . + an*D2(Fo,n).

In another embodiment, to calculate the second dose D(Fp), third doses De (De(Fo,1), De(Fo,2), ..., De(Fo,n)), which are the differences between doses calculated using the first set of fluence maps Fo and the first dose prediction model 151 and doses calculated using the first set of fluence maps Fo and the second dose prediction model 152, are accessed. A fourth dose D1(Fp) is calculated using the second fluence map Fp and the first dose prediction model 151, and the fourth dose is summed with the products of multiplying the set of scalars and the third doses De to calculate the second dose: D(Fp)=D1(Fp)+a1*De(Fo,1)+a2*De(Fo,2)+. . . + an*De(Fo,n).

In block 610, a final radiation treatment plan including a final fluence map is selected from a sample set of treatment plans that includes at least a first radiation treatment plan based on the first set of fluence maps Fo and a second radiation treatment plan based on the second fluence map Fp. The final fluence map can be converted into a set of leaf sequence settings that control movement of an MLC during radiation treatment.

In summary, embodiments according to the invention improve the field of radiation treatment planning specifically and the field of radiation therapy in general. Embodiments according to the invention allow more effective treatment plans to be generated quickly, which can be of critical importance considering the urgency of beginning radiation therapy when a patient is diagnosed with a disease such as cancer. Also, embodiments according to the invention help improve the functioning of computer systems because fewer computational resources are needed and consumed to develop a plan, meaning also that computer resources are freed up to perform other tasks.

Embodiments according to the invention are thus described. These embodiments can be used to plan different types of external beam radiotherapy other than IMRT including, for example, image-guided radiotherapy (IGRT), RapidArc™ radiotherapy, stereotactic body radiotherapy (SBRT), and stereotactic ablative radiotherapy (SABR).

Although the subject matter has been described ire language specific to structural features and/or methodological acts, it is to be understood that the subject matter defined in the appended claims is not necessarily limited to the specific features or acts described above. Ratner, the specific, features and acts described above are disclosed, as example forms of implementing the claims.

What claimed is:

1. A computing system comprising:
a central processing unit (CPU); and
memory coupled to the CPU and having stored therein instructions that, when executed by the computing system, cause the computing system to execute operations associated with generating a radiation treatment plan, the operations comprising:
accessing a first dose calculated using first set of fluence maps and a first dose prediction model;
accessing a second fluence map;
projecting the second fluence map onto the first set of fluence maps to determine a set of scalars and a residual value; and
when the residual value satisfies a criterion, calculating a second dose using the first dose prediction model, the set of scalars, and the second fluence map, and wherein when the residual value does not satisfy the criterion, calculating the second dose using a second dose prediction model and the second fluence map.

2. The computing system of claim 1, wherein the operations further comprise accessing a set of third doses calculated using the first set of fluence maps and the second dose prediction model;
wherein said calculating a second dose using the first dose prediction model, the set of scalars, and the second fluence map comprises:
calculating a fourth dose using the first dose prediction model and the residual value; and
summing the fourth dose and products of multiplying the set of scalars and the set of third doses.

3. The computing system of claim 1, wherein the operations further comprise accessing a set of third doses comprising differences between doses calculated using the first set of fluence maps and the first dose prediction model and doses calculated using the first set of fluence maps and the second dose prediction model;

wherein said calculating a second dose using the first dose prediction model, the set of scalars, and the second fluence map comprises:
calculating a fourth dose using the second fluence map and the first dose prediction model; and
summing the fourth dose and products of multiplying the set of scalars and the third set of doses.

4. The computing system of claim 1, wherein the criterion comprises a threshold value or magnitude of the residual value.

5. The computing system of claim 1, wherein the criterion comprises a threshold value for a normalized value of the residual value.

6. The computing system of claim 1, wherein the second dose prediction model is more accurate and utilizes more computational resources than the first dose prediction model.

7. The computing system of claim 1, wherein the operations further comprise;
selecting a final fluence map for radiation treatment, wherein the final fluence map is selected from a plurality fluence maps comprising at least the first set of fluence maps and the second fluence map; and
converting the final fluence map into leaf sequence settings that control movement of a multileaf collimator during the radiation treatment.

8. A computing system comprising:
a central processing unit (CPU); and
memory coup ed to the CPU and having stored therein instructions that, when executed by the computing system, cause the computing system to execute operations associated with generating a radiation treatment plan, the operations comprising:
calculating first doses using a first set of fluence maps and a first dose prediction model;
accessing a second fluence map;
projecting the second fluence map onto the first set of fluence maps to determine a set of scalars and a residual value; and
selecting, based on the residual value, a dose prediction model to calculate a second dose using the second fluence map, wherein when the residual value satisfies a criterion, then the second dose is calculated using the first dose prediction model and wherein when the residual value does not satisfy the criterion, then the second dose calculated using a second dose prediction model, wherein the second dose prediction model calculates the second doses more accurately than the first dose prediction model.

9. The computing system of claim 8, wherein the operations further comprise calculating third doses using the first set of fluence maps and the second dose prediction model, wherein further when the residual value satisfies the criterion then the second dose is calculated by:
calculating a fourth dose using the first dose prediction model and the residual value; and
summing the fourth dose and products of multiplying the set of scalars and the third doses.

10. The computing system of claim 8, wherein the operations further comprise calculating third doses comprising differences between doses calculated using the first set of fluence maps and the first dose prediction model and doses calculating using the first set of fluence maps and the second dose prediction model wherein further when the residual value satisfies the criterion then the second doses are calculated by:

calculating a fourth dose using the second fluence map and the first dose prediction model; and summing the fourth dose and products of multiplying the set of scalars and the third doses.

11. The computing system of claim 8, wherein the criterion comprise a threshold value for a magnitude of the residual value.

12. The computing system of claim 8, wherein the criterion comprises a threshold value for a normalized value of the residual value.

13. The computing system of claim 8, wherein the operations further comprise:

selecting a final fluence map for radiation treatment, wherein the final fluence map is selected from a plurality of fluence maps comprising at least the first set of fluence maps and the second fluence map; and converting the final fluence map into leaf sequence settings that control movement of a multileaf collimator during the radiation treatment.

14. A computer-implemented method for radiation treatment planning, the method comprising:

generating a first radiation treatment plan comprising a first set of fluence map, wherein the first radiation treatment plan is generated using a first model that calculates first doses using the first set of fluence maps;

generating a second radiation treatment plan comprising a second fluence map, wherein the second radiation treatment plan is generated by:

projecting the second fluence map onto the first, set of fluence maps to determine a set of scalars d a residual value; and when the residual value satisfies a criterion, using the first model to calculate a second dose using the set of scalars and the second fluence map, and when the residual value does not satisfy the criterion, using a second model to calculate the second dose using the second fluence map; and selecting a final radiation treatment plan from a plurality of radiation treatment plans, wherein the plurality of radiation treatment plans comprises at least the first and second radiation treatment plans.

15. The method of claim 14, further comprising, accessing third doses calculated using the first set of fluence maps and the second dose prediction model;

wherein calculating the second dose using the first dose prediction model, the set of scalars, and the second set of fluence maps comprises:

calculating a fourth dose using the first dose prediction model and the residual value, and summing the fourth dose and products of multiplying the set of scalars and the third doses.

16. The method of claim 14, further comprising accessing third doses comprising differences between doses calculated using the first set of fluence maps and the first dose prediction model and doses calculating using the first set of fluence maps and the second dose prediction model;

wherein calculating the second dose using the first dose prediction model, the set of scalars, and the second set of fluence maps comprises:

calculating a fourth dose using the second fluence map and the first dose prediction model; and summing the fourth dose and products of multiplying the set of scalars and the third doses.

17. The method of claim 14, wherein the criterion comprises a threshold value for a magnitude of the residual value.

18. The method of claim 14, wherein the criterion comprises a threshold value for normalized value of the residual value.

19. The method of claim 14, wherein the second dose prediction model is more accurate and utilizes more computational resources than the first dose prediction model.

20. The method of claim 14, further comprising:

selecting a final fluence map for the final radiation treatment plan, wherein the final fluence map is selected from a plurality of fluence maps comprising at least the first set of fluence maps and the second fluence map; and converting the final fluence map into leaf sequence settings that control movement of a multileaf collimator.

* * * * *